(12) United States Patent
Lou et al.

(10) Patent No.: US 9,664,587 B2
(45) Date of Patent: May 30, 2017

(54) METHOD AND DEVICE FOR BALANCING CT GANTRY

(71) Applicant: Shenyang Neusoft Medical Systems Co., Ltd., Shenyang (CN)

(72) Inventors: Shanshan Lou, Shenyang (CN); Junfang Ma, Shenyang (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 276 days.

(21) Appl. No.: 14/513,219

(22) Filed: Oct. 14, 2014

(65) Prior Publication Data
US 2015/0185107 A1 Jul. 2, 2015

(30) Foreign Application Priority Data
Dec. 31, 2013 (CN) .......................... 2013 1 0752409

(51) Int. Cl.
*G01M 1/36* (2006.01)
*G01N 23/04* (2006.01)

(52) U.S. Cl.
CPC ............ *G01M 1/36* (2013.01); *G01N 23/046* (2013.01)

(58) Field of Classification Search
CPC ................................ G01M 1/36; G01N 23/046
USPC .......................................................... 73/468
See application file for complete search history.

(56) References Cited

U.S. PATENT DOCUMENTS

| | | | | |
|---|---|---|---|---|
| 6,748,806 B2 * | 6/2004 | Halsmer | ............... | A61B 6/4441 378/162 |
| 6,890,100 B2 * | 5/2005 | Reznicek | ................ | G01M 1/32 378/15 |
| 7,236,855 B2 * | 6/2007 | Danz | ..................... | A61B 6/035 700/279 |
| 2009/0046835 A1 | 2/2009 | Kodama et al. | | |

FOREIGN PATENT DOCUMENTS

| | | |
|---|---|---|
| CN | 1575767 A | 2/2005 |
| CN | 1828250 A | 9/2006 |
| CN | 102772218 A | 11/2012 |
| CN | 102809464 A | 12/2012 |
| CN | 203191158 U | 9/2013 |
| WO | 2012095773 A2 | 7/2012 |

\* cited by examiner

*Primary Examiner* — John Chapman, Jr.
(74) *Attorney, Agent, or Firm* — Kilpatrick Townsend & Stockton LLP

(57) ABSTRACT

A method and a device for balancing a CT gantry device are provided. The method includes: obtaining a fluctuation chain of pulses generated in one revolution of the CT gantry and obtained when the CT gantry collects data; obtaining an eccentric angle of a center of mass according to the fluctuation chain, and calculating a magnitude of imbalance; and adjusting weight at a weight counterbalancing position according to the eccentric angle and the magnitude of imbalance, to locate the center of mass at the rotation center. The device includes a data collection unit for collecting a fluctuation chain, and a processor for obtaining an eccentric angle of a center of mass, and calculating a magnitude of imbalance; and the processor adjusts weight at the weight counterbalancing position according to the eccentric angle and the magnitude of imbalance, to locate the center of mass at the rotation center.

11 Claims, 3 Drawing Sheets

METHOD AND DEVICE FOR BALANCING CT GANTRY

The present application claims the benefit of priority to Chinese Patent Application No. 201310752409.4, titled "METHOD AND DEVICE FOR BALANCING CT GANTRY", filed with the Chinese State Intellectual Property Office on Dec. 31, 2013, the entire disclosure of which is incorporated herein by reference.

TECHNICAL FIELD

The present application relates to the technical field of medical equipment, and in particular to a method for balancing a Computed Tomography (CT) gantry.

BACKGROUND

A rotary gantry of a CT machine is installed with several components, thus the equilibrium of mass distribution should be taken into consideration in the mechanical design, to ensure that the rotary gantry of the CT machine may rotate evenly, thereby obtaining high-quality images.

Reference is made to FIG. 1, which is a schematic view showing an assembling structure of a CT gantry according to an embodiment in the conventional technology.

In practice, errors of various components in the mechanical manufacture and installation processes cause the imbalance of mass distribution of the gantry, that is, a centre of mass M of the gantry deviates from a rotation center, and as shown in FIG. 1, such eccentricity may generate a resultant force $F_r$ at the centre of mass M.

$F_r$ may be decomposed into a force $F_d$ in a diametrical direction and a force $F_t$ in a tangential direction. The periodic variation of $F_r$ will cause the periodic variation of both of the two force components, and the periodic variation of the force component $F_t$ will apply a periodic moment on the gantry during the rotation of the gantry, and in this case, the rotation velocity of the gantry is nonuniform. The image quality will be affected when the force $F_r$ reaches a certain value, and the vibration caused by the force $F_r$ may adversely affect the service life of a bearing. Therefore, a weight counterbalancing position is required to be arranged on the gantry, and counter weight at the weight counterbalancing position is adjusted to locate the centre of mass of the rotary part of the gantry at the rotation center of the gantry to the greatest extent, so as to reduce the influence caused by the deviation of the centre of mass.

In view of the above issues, in a Chinese patent No. 200410071323.6 titled "SYSTEM AND METHOD FOR BALANCING CT GANTRY", imbalance information is collected by a specific sensor so as to perform weight counterbalance properly. In a Chinese patent No. 201110145218.2 titled "DYNAMIC BALANCE MEASUREMENT METHOD AND DEVICE AND CT MACHINE HAVING THE SAME", weight counterbalance is performed in an axial direction of the CT machine based on measurements of dynamic balance.

Therefore, in the conventional technology, before performing weight counterbalance, additional devices other than the CT machine are generally required to obtain imbalance information of the CT machine. Due to the additional devices, the structure of the CT machine is more complicated. Furthermore, additional measurement and transmission steps are further required, which makes the procedure for balancing the CT gantry more complicated.

Thus, the technical problem to be solved by those skilled in the art is to design a method and a device for balancing the CT gantry, which may perform weight counterbalance based on imbalance information obtained without adding an additional device.

SUMMARY

A method for balancing a CT gantry is provided according to the present application, in which imbalance information may be obtained while the CT gantry collects data, thus it is not necessary to collect imbalance information separately, which simplifies the detection procedure.

A device for balancing a CT gantry is further provided according to the present application, in which imbalance information may be obtained without adding an additional device, thus weight counterbalance may be performed properly to realize the balance of the CT gantry.

To address the above technical issues, a method for balancing a CT gantry is provided according to the present application, which includes the following steps:

11) obtaining a fluctuation chain of pulses generated in one revolution of the CT gantry and obtained when the CT gantry collects data;

12) obtaining an eccentric angle of a center of mass deviating from a rotation center according to the fluctuation chain, and calculating a magnitude of imbalance; and 13) adjusting weight at a weight counterbalancing position according to the eccentric angle and the magnitude of imbalance, to locate the center of mass at the rotation center.

The CT gantry collects data during the rotation of the gantry, and the collected data includes a fluctuation chain of pulses generated in one revolution of the CT gantry. According to the method of the present application, imbalance information of the gantry is provided by the fluctuation chain, and weight counterbalance may be adjusted according to the imbalance information so as to realize the balance setting of the CT gantry. Compared to the conventional technology that the imbalance information of the gantry is provided by using additional parameters, the imbalance information is provided by the fluctuation chain obtained in one revolution of the CT gantry according to the method of the present application, thus, the collection of the imbalance information may be accomplished while the CT gantry collects data, which further simplifies the operation procedure, and improves the efficiency of weight counterbalance and the convenience of the operation. Meanwhile, the imbalance information obtained from the data collected by the CT gantry has an improved accuracy, therefore, the weight counterbalance of the gantry may be performed more accurately and the reliability of the balance setting of the gantry may be improved.

Preferably, the step 11) includes the following steps:

performing sampling once each time the gantry rotates by a constant angle, obtaining a curve of a pulse generated in each sampling, and connecting successively curves corresponding to respective angles in a rotation direction of the gantry to form the fluctuation chain.

The CT gantry may employ a uniform angular sampling, and one revolution is uniformly divided into several small parts. The sampling is performed once each time the gantry rotates by a constant angle, and a corresponding pulse curve is obtained. The duration required for the gantry rotating by respective constant angles varies due to the imbalance of the gantry, and the duration of the pulse corresponds to a sampling time, thus, during one revolution of the gantry, pulse curves obtained in respective samplings are curves having different lengths, which forms the fluctuation chain. The above process has a higher sampling rate and thus the effectiveness of the collected data may be guaranteed.

Preferably, the data collected during the sampling of the CT gantry is data collected without X-ray exposure, which may reduce radiation and save energy.

Preferably, the method further includes the following step 00) before the step 11):

adjusting a torque voltage of a motor configured to drive the gantry to rotate, to enable the rotation of the gantry to reach a steady state.

The rotation state of the gantry may be adjusted before collecting data, to maintain the rotation velocity of the gantry in a certain range, thereby guaranteeing the authenticity and effectiveness of the collected data.

Preferably, the step 12) includes the following steps:

121) performing a Fourier transform on the fluctuation chain, and obtaining a cosine function of the fluctuation chain by remaining a fundamental harmonic component and assuming other harmonic components to be zero, and a phase angle of the cosine function being the eccentric angle; and 122) calculating the magnitude of imbalance according to the cosine function and the eccentric angle.

Preferably, in the step 122), the magnitude of imbalance is represented by the product of a mass (m) of the gantry and an eccentric distance (r), and is obtained through the following equation:

$$|\vec{P}| = \frac{2\pi J(t_i - t_{i+1})}{gNt_{i+1}t_i^2 \sin\alpha}$$

wherein $\vec{P}$ is an imbalance vector, J is a rotational inertia, N is a number of constant angles by which the gantry rotates in one revolution, $t_i$ is a duration required for the gantry rotating by the ith constant angle, $t_{i+1}$ is a duration required for the gantry rotating by the (i+1)th constant angle, g is the acceleration of gravity, and $\alpha$ is the eccentric angle.

The magnitude of imbalance may be calculated based on the rotational inertia according to the above equation, which simplifies the calculation process, and the calculation may be accomplished by just using the data collected by the CT gantry.

A device for balancing a CT gantry is further provided according to the present application, the CT gantry has a data collection unit for collecting data and a weight counterbalancing position for balancing the CT gantry, wherein the device includes a processor in signal connection with the data collection unit; the data collection unit is configured to collect a fluctuation chain of pulses generated in one revolution of the gantry; the processor is configured to obtain an eccentric angle of a center of mass deviating from a rotation center according to the fluctuation chain, and calculate a magnitude of imbalance. The processor is configured to adjust weight at the weight counterbalancing position according to the eccentric angle and the magnitude of imbalance, to locate the center of mass at the rotation center.

The device according to the present application collects the imbalance information by using the data collection unit of the CT gantry. Compared to the conventional technology that an additional device is required, the device according to the present application has a simple structure and simplifies the whole structure of the gantry, and is easy to operate. More importantly, the data collected by the data collecting unit has a higher accuracy, which may provide the imbalance information of the gantry more accurately, thus weight counterbalance may be performed properly which increases the accuracy of the balance of the gantry.

Preferably, the device further includes a detector for detecting a rotation velocity of the gantry in real time, wherein the detector is in signal connection with the processor, and the processor is configured to adjust a torque voltage of a motor according to the rotation velocity of the gantry, to enable the rotation of the gantry to reach a steady state.

The processor according to the present application may be further configured to control the torque voltage of the motor to control the gantry to reach the steady state, thereby improving the accuracy of subsequent data collection.

DETAILED DESCRIPTION

A method for balancing a CT gantry is provided according to the present application, in which imbalance information may be obtained while the CT gantry collects data, thus it is not necessary to collect imbalance information separately, which simplifies the detection procedure.

A device for balancing a CT gantry is further provided according to the present application, in which imbalance information may be obtained without adding an additional device, thus weight counterbalance may be performed properly to realize the balance of the CT gantry.

For those skilled in the art to better understand the technical solutions of the present application, the present application will be further described in detail in conjunction with the drawings and the embodiments.

Figure 1:
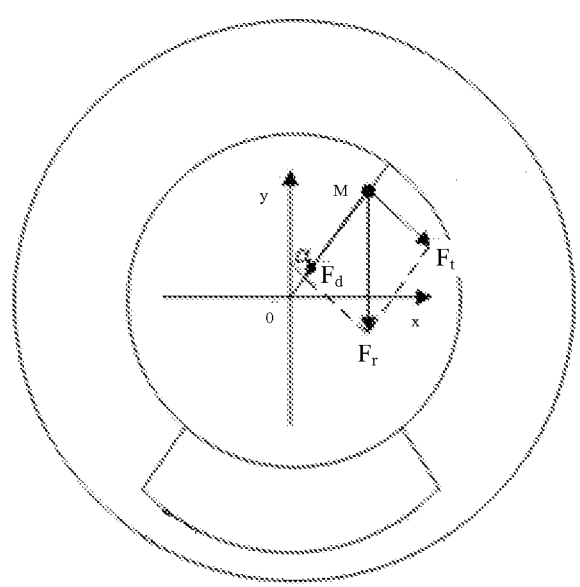
FIG. 1 is a schematic view showing an assembling structure of a CT gantry according to an embodiment in the conventional technology.
Figure 2:
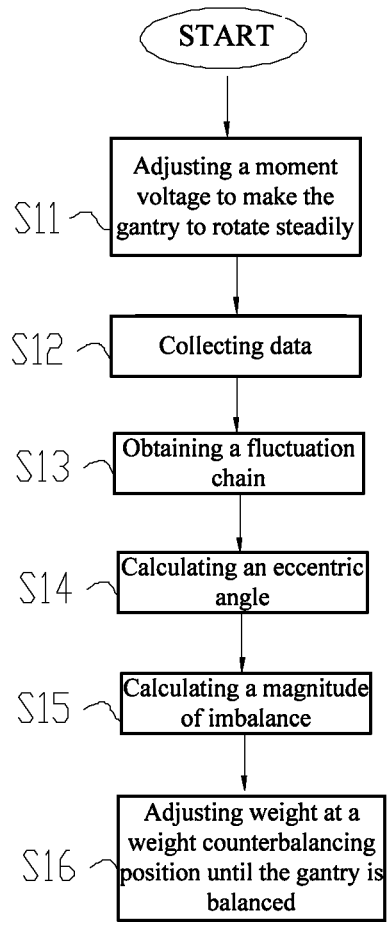
FIG. 2 is a flow chart of a method according to an embodiment of the present application.

Reference is made to FIG. 2, which is a flow chart of the method according to an embodiment of the present application.

It should be understood by those skilled in the art that, the CT gantry collects data during its rotation, and in the method for balancing the CT gantry according to the present application, imbalance information is obtained by using the data collected during the rotation of the CT gantry, and in turn weight counterbalance is performed based on the obtained imbalance information to locate a center of mass of the gantry at a rotation center of the gantry, thereby eliminating the imbalance factor.

The method according to the present application includes the following steps.

S11 may include adjusting a torque voltage of a motor to make the gantry to rotate in a steady state. The motor for driving the gantry to rotate operates in a "moment" mode by the setting of software. During the rotation of the gantry, a rotation velocity of the gantry is continuously read, and a control voltage of the motor is changed in real time, thus the rotation velocity of the gantry may be maintained within a certain range, and the rotation of the gantry may reach a steady state.

S12 may include collecting data. After the rotation of the gantry has reached the steady state, the system sends an instruction for collecting data, and the CT gantry collects data, wherein the collected data may be data collected without X-ray exposure.

S13 may include obtaining a fluctuation chain. The fluctuation chain of pulses generated in one revolution of the CT gantry is obtained from the data collected by the CT gantry.

S14 may include calculating an eccentric angle α of a center of mass deviating from a rotation center according to the fluctuation chain. A Fourier transform may be performed on the fluctuation chain, a fundamental harmonic component is remained, and other harmonic components are assumed to be zero, thereby obtaining a cosine function of the fluctuation chain. A phase angle of the cosine function is the eccentric angle.

S15 may include calculating a magnitude of imbalance. $\vec{P}$ refers to an imbalance vector, a magnitude of the vector $\vec{P}$ is the magnitude of imbalance, and the magnitude of the vector $\vec{P}$ may be represented by the product of a mass m of the gantry and an eccentric distance r of the center of mass deviating from the rotation center, and may be obtained through the following equation:

$$|\vec{P}| = \frac{2\pi J(t_i - t_{i+1})}{gNt_{i+1}t_i^2 \sin\alpha} \quad (1)$$

wherein, $\vec{P}$ is the imbalance vector, J is a rotational inertia, N is a number of constant angles by which the gantry rotates in one revolution, $t_i$ is a duration required for the gantry rotating by the ith constant angle, $t_{i+1}$ is a duration required for the gantry rotating by the (i+1)th constant angle, g is the acceleration of gravity, and α is the eccentric angle. The values of $t_i$ and $t_{i+1}$ may be calculated from the cosine function transformed from the fluctuation chain.

S16 may include adjusting a weight on a weight counterbalancing position according to the eccentric angle α and the magnitude of imbalance, to locate the center of mass at the rotation center, thereby realizing the balance of the gantry.

Figure 3:
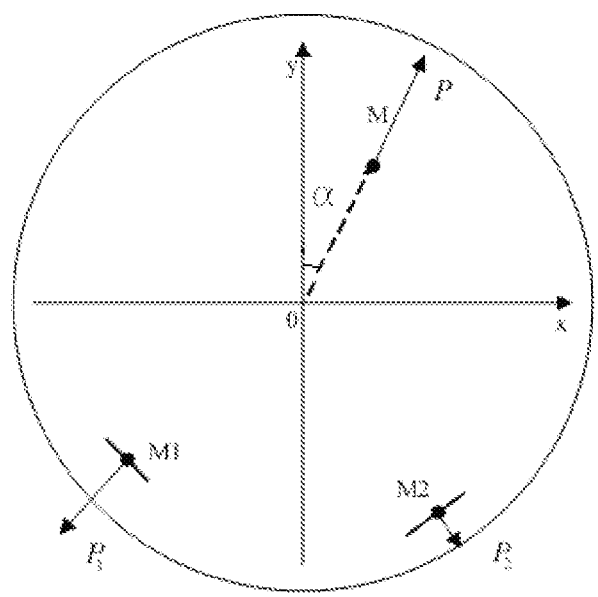
FIG. 3 is a principle diagram of weight counterbalance.

Reference is further made to FIG. 3, which is a principle diagram of weight counterbalance.

According to the background, the nonuniform rotation velocity and the vibration of the gantry are caused by the force components $E_d$ and $F_t$ (M=$F_t$r, wherein M is a moment) generated at the eccentric position of the gantry, and both force components relate to the distance r between the center of mass and the rotation center, therefore the problems of the nonuniform rotation velocity and the vibration of the gantry may be solved by adjusting the center of mass of the gantry to the rotation center of the gantry (that is, r=0). The position of the center of mass and the magnitude of the resultant external force may be adjusted by increasing or decreasing the weight at the weight counterbalancing position. Thus, the vector $\vec{P}$ may be defined to represent the eccentric degree of an object, and a magnitude thereof may be defined as:

$$|\vec{P}| = mr \quad (2)$$

Equation (2) represents the magnitude of eccentricity, and its direction is a radially outward direction; an angle of the vector is defined as the eccentric angle of the center of mass with respect to the rotation center, i.e., the above eccentric angle α, when the object is at a fixed position. Therefore the weight counterbalance may be achieved by eliminating the influence caused by the imbalance vector $\vec{P}$. The principle diagram of weight counterbalance is shown in FIG. 3.

As shown in FIG. 3, since the imbalance of the gantry exists in a plane perpendicular to the rotation axis, the plane perpendicular to the rotation axis of the gantry is taken as the coordinate plane and is divided into four regions by an X axis and a Y axis. The center of mass M of the gantry is assumed to be in one of the regions. Due to the eccentricity, an imbalance vector $\vec{P}$ is generated at the center of mass M of the gantry during the rotation of the gantry. Therefore, two weight counterbalancing positions may be arranged in two regions opposite to the direction of the imbalance vector $\vec{P}$, i.e. the weight counterbalancing position M1 and the weight counterbalancing position M2 as shown in FIG. 3. Two vectors $\vec{P}_1$ and $\vec{P}_2$ are generated by adding certain weight at the two weight counterbalancing positions respectively.

The imbalance vector $\vec{P}$ is balanced out when $\vec{P}+\vec{P}_1+\vec{P}_2=0$. In this case:

$$\vec{P}\cos\alpha + \vec{P}_1\cos\alpha_1 + \vec{P}_2\cos\alpha_2 = 0 \quad (3)$$

$$\vec{P}\sin\alpha + \vec{P}_1\sin\alpha_1 + \vec{P}_2\sin\alpha_2 = 0 \quad (4)$$

That is, the center of mass of the gantry is at the rotation center, wherein $\alpha_1$ and $\alpha_2$ are the eccentric angles of the weight counterbalancing positions M1 and M2 with respect to the rotation center respectively. In actual application, the weight counterbalancing positions M1 and M2 are fixed, thus, $\alpha_1$ and $\alpha_2$ are known parameters, and only $\vec{P}_1$, $\vec{P}_2$, $\vec{P}$ and α are unknown parameters. $\vec{P}_1$ and $\vec{P}_2$ may be calculated when the values of $\vec{P}$ and α are obtained, thus weight counterbalance may be performed properly.

Thus, the magnitude of the vector $\vec{P}$ and the eccentric angle α are required to be obtained firstly according to the method of the present application. Therefore, according to the method of the present application, $\vec{P}$ and α are obtained through the above steps S11 to S15, and finally in the step S16, the weights on the two weight counterbalancing positions are calculated through the above equations (3) and (4), in this case, the weights on the two weight counterbalancing positions are adjusted to locate the center of mass of the gantry at the rotation center.

Figure 4:
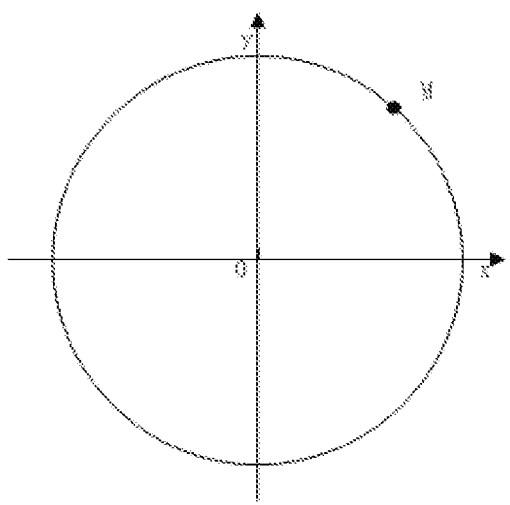
FIG. 4 is a principle diagram of sampling in the method according to the present application.

Reference is made to FIG. 4, which is a principle diagram of sampling in the method according to the present application.

In the step S12, the gantry performs uniform angular sampling. One revolution is uniformly divided into N angles, and the sampling is performed once each time the gantry rotates by a constant angle, and a pulse generated in each sampling is obtained to form a pulse curve. Curves corresponding to respective angles are connected successively along the rotational direction of the gantry to form the fluctuation chain, and the fluctuation chain represents the lengths of the pulses generated in one revolution of the CT gantry.

The value of N depends on multiple factors, such as the precision of image construction, the size of data and the speed of calculation. Generally, N has a larger value to divide the circumference into more small angles, thereby improving the precision of sampling.

In the above procedure, one pulse is generated in each sampling, and the pulse determines a start time and an end time of the sampling, i.e., the duration of the pulse is the duration of the sampling, and the duration of the pulse corresponds to the time duration required for the rotation. In the rotation of the gantry, because of the imbalance of the gantry, the gantry rotates slowly at some positions, thus taking more time to rotate by the constant angle; and the gantry rotates fast at some angles, thus taking less time to rotate by the constant angle. Therefore, the pulse fluctuations obtained in one revolution of the CT gantry are connected successively to form a curve having different lengths, and the obtained curve is the fluctuation chain. Since the fluctuation chain is caused by the imbalance of the gantry, the fluctuation chain may represent the imbalance of the gantry. In the method of the present application, the imbalance information of the gantry is obtained by using the fluctuation chain.

The driving force applied to the gantry from the motor is constant when the motor is in the "moment" mode. However, since the gantry is also influenced by the force $F_t$ in the tangential direction caused by the eccentricity, and the velocity of the gantry generates a periodic fluctuation under the action of the moment generated by $F_t$. The greater the amplitude of the fluctuation is, the greater the magnitude of the moment is. Such fluctuation may be represented by the fluctuation chain. An equation of the cosine function may be obtained by performing a Fourier transform on the fluctuation chain:

$$t(n) = c_0 + A\cos\left(2\pi\frac{n}{N} + \theta\right) \quad (5)$$

wherein, t is the curve of the fluctuation chain, n is a sampling times, A is an amplitude, $\theta$ is an initial phase, and $c_0$ is a deviation value in the direction of the Y axis. According to the equation (5), the fluctuation chain varies periodically, and t has the maximum amplitude A when $2\pi n/N+\theta=2\pi$. Since t is inversely proportional to the rotation velocity, t having the maximum value means that the velocity has the minimum value, and the minimum velocity means that the center of mass has just passed through the Y axis in FIG. 3, and Y>0. That is, $\theta$ may be used to determine the eccentric position of the center of mass, i.e. it may be considered that $\theta=\alpha$, thus the eccentric angle $\alpha$ is obtained as described in the step S14.

Further, in the step S15, the magnitude of the vector $\vec{P}$ is required to be calculated. Since the variation of the moment at the center of mass M is only influenced by the gravity in the rotation process, the resultant external moment may be represented by:

$$M = Ja = mgr \sin \theta \quad (6)$$

wherein, M is the resultant external moment, a is an angular acceleration, g is the acceleration of gravity, and J is a moment of inertia. Assuming that $\theta=\alpha$, the magnitude of the imbalance vector at the eccentric position may be obtained by:

$$|\vec{P}| = mr = \frac{Ja}{g\sin\alpha} \quad (7)$$

In the equation (7), only $\alpha$ is an unknown parameter, and J is a constant. Assuming that the center of mass is located in the ith sampling region, since the angle $\phi$ is constant in all the sampling regions, i.e. $\phi=2\pi/N$, and $\phi$ has a very small value, an initial angular velocity of the ith sampling region may be considered as $\omega_i=\phi/t_i$, and a terminal angular velocity of the ith sampling region may be considered as $\omega_{i+1}=\phi/t_{i+1}$, thus $$a = \frac{\omega_{i+1} - \omega_i}{t_i} = \frac{2\pi(t_i - t_{i+1})}{Nt_{i+1}t_i^2} \quad (8)$$

The equation (1) may be obtained by substituting the equation (8) into the equation (7). Since each variable in the equation (1) is known, the vector $\vec{P}$ may be calculated. Then $\vec{P}_1$ and $\vec{P}_2$, which are the weights to be increased or decreased at the two weight counterbalancing positions, may be calculated by substituting the above calculated $\alpha$ and $\vec{P}$ into the equations (3) and (4), thus the weights at the weight counterbalancing positions may be adjusted in the step S16 to locate the center of mass of the gantry at its rotation center.

It should be understood by those skilled in the art that, the setting in the step S11 may stabilize the rotation state of the gantry. Compared to the manner that the data collection is performed once the gantry starts to rotate, the effectiveness of data collection may be improved by performing the step S11. In the step S12, the imbalance information may be collected without X-ray exposure since X-ray exposure has little influence on the imbalance of the gantry, thus the radiation may be reduced.

It should be noted that, the steps S12 and S13 are processes for collecting data. The fluctuation chain obtained in the step S13 is already obtained in the step S12 when data collection is performed, and the step S13 is only a process for extracting data for subsequent usage, which is the difference between the present application and the conventional technology. In the conventional technology, a detection device independent of the operating system of the CT gantry is required to perform a detecting process to obtain the imbalance information, however, according to the present application, the imbalance information is obtained from the fluctuation chain in the data collected by the CT gantry itself, thus the whole process is relatively simple and fast, and the obtained data has a higher accuracy, which may facilitate performing the subsequent weight counterbalance properly.

In addition, according to the present application, after the fluctuation chain is obtained, a Fourier transform is performed on the fluctuation chain to obtain the cosine function of the fluctuation chain, thereby obtaining the eccentric angle $\alpha$. Then the vector $\vec{P}$ is calculated based on the cosine function and the eccentric angle $\alpha$. That is, only in the case that the fluctuation chain is processed by using the Fourier transform, the above step S14 is performed firstly, and then the step S15 is performed. In other processing methods, the sequence of the step S14 and the step S15 is not limited and may be adjusted as required to obtain the values of $\vec{P}$ and $\alpha$.

A device for balancing a CT gantry is further provided according to the present application. The CT gantry is provided with a data collection unit for collecting data, and in the rotation of the gantry, the data collection unit collects data. The CT gantry is further provided with a weight counterbalancing position for balancing the gantry. The device for balancing the CT gantry according to the present application includes a processor in signal connection with the data collection unit. When collecting data, the data collection unit may obtain a fluctuation chain of pulses generated in one revolution of the CT gantry. The processor obtains an eccentric angle α of a center of mass deviating from a rotation center based on the fluctuation chain and calculates a magnitude of the imbalance vector $\vec{P}$. The processor adjusts the weight at the weight counterbalancing position according to the eccentric angle α and the magnitude of the imbalance vector $\vec{P}$, so as to locate the center of mass at the rotation center.

The device according to the present application collects the imbalance information by using the data collection unit of the CT gantry. Compared to the conventional technology that an additional device is required, the device according to the present application has a simple structure and simplifies the whole structure of the gantry, and is easy to operate. More importantly, the data collected by the data collecting unit has a higher accuracy, which may provide the imbalance information of the gantry more accurately, thus weight counterbalance may be performed properly which increases the accuracy of the balance of the gantry.

It is conceivable that, the device according to the present application may further include a detector for detecting the rotation velocity of the gantry in real time. The detector is in signal connection with the processor, and the processor adjusts a torque voltage of a motor according to the rotation velocity of the gantry, to enable the rotation of the gantry to reach a steady state, thereby improving the accuracy of subsequent data collection.

The signal connection refers to a connection manner in which signal is transmitted in a wired or wireless manner.

A method and a device for balancing a CT gantry provided by the present application are described in detail hereinbefore. The principle and the embodiments of the present application are illustrated herein by specific examples. The above description of examples is only intended to help understanding the concept of the present application. It should be noted that, for the person skilled in the art, a few of modifications and improvements may be made to the present application without departing from the principle of the present application, and these modifications and improvements are also deemed to fall into the scope of the present application defined by the claims.

The invention claimed is:

1. A method for balancing a Computed Tomography (CT) gantry comprising the following steps:
   1) obtaining a fluctuation chain of pulses generated in one revolution of the CT gantry and obtained when the CT gantry collects data;
   2) obtaining an eccentric angle of a center of mass deviating from a rotation center according to the fluctuation chain, and calculating a magnitude of imbalance; and
   3) adjusting weight at a weight counterbalancing position according to the eccentric angle and the magnitude of imbalance, to locate the center of mass at the rotation center; and
   wherein step 1) comprises: performing sampling once each time the gantry rotates by a constant angle, obtaining a curve of a pulse generated in each sampling, and connecting successively curves corresponding to respective angles in a rotational direction of the gantry to form the fluctuation chain.

2. The method for balancing the CT gantry according to claim 1, wherein the data collected during the sampling of the CT gantry is data collected without X-ray exposure.

3. The method for balancing the CT gantry according to claim 2, wherein the step 2) comprises the following steps:
   21) performing a Fourier transform on the fluctuation chain, and obtaining a cosine function of the fluctuation chain by remaining a fundamental frequency component and assuming other harmonic components to be zero, and a phase angle of the cosine function being the eccentric angle; and
   22) calculating the magnitude of imbalance according to the cosine function and the eccentric angle.

4. The method for balancing the CT gantry according to claim 3, wherein in the step 22), the magnitude of imbalance is represented by the product of a mass (m) of the gantry and an eccentric distance (r), and is obtained through the following equation:

$$|\vec{P}| = \frac{2\pi J(t_i - t_{i+1})}{gNt_{i+1}t_i^2 \sin\alpha}$$

Wherein, $\vec{P}$ is an imbalance vector, J is a rotational inertia, N is a number of constant angles by which the gantry rotates in one revolution, $t_i$ is a duration required for the gantry rotating by the ith constant angle, $t_{i+1}$ is a duration required for the gantry rotating by the (i+1)th constant angle, g is the acceleration of gravity, and α is the eccentric angle.

5. The method for balancing the CT gantry according to claim 1, further comprising the following step 0) before the step 1):
   adjusting a torque voltage of a motor configured to drive the gantry to rotate, to enable the rotation of the gantry to reach a steady state.

6. The method for balancing the CT gantry according to claim 5, wherein the step 2) comprises the following steps:
   21) performing a Fourier transform on the fluctuation chain, and obtaining a cosine function of the fluctuation chain by remaining a fundamental frequency component and assuming other harmonic components to be zero, and a phase angle of the cosine function being the eccentric angle; and
   22) calculating the magnitude of imbalance according to the cosine function and the eccentric angle.

7. The method for balancing the CT gantry according to claim 6, wherein in the step 22), the magnitude of imbalance is represented by the product of a mass (m) of the gantry and an eccentric distance (r), and is obtained through the following equation:

$$|\vec{P}| = \frac{2\pi J(t_i - t_{i+1})}{gNt_{i+1}t_i^2 \sin\alpha}$$

Wherein, $\vec{P}$ is an imbalance vector, J is a rotational inertia, N is a number of constant angles by which the gantry rotates in one revolution, $t_i$ is a duration required for the gantry rotating by the ith constant angle, $t_{i+1}$ is a duration required for the gantry rotating by the (i+1)th constant angle, g is the acceleration of gravity, and α is the eccentric angle.

8. The method for balancing the CT gantry according to claim 1, wherein the step 2) comprises the following steps:

21) performing a Fourier transform on the fluctuation chain, and obtaining a cosine function of the fluctuation chain by remaining a fundamental frequency component and assuming other harmonic components to be zero, and a phase angle of the cosine function being the eccentric angle; and 22) calculating the magnitude of imbalance according to the cosine function and the eccentric angle.

9. The method for balancing the CT gantry according to claim 8, wherein in the step 22), the magnitude of imbalance is represented by the product of a mass (m) of the gantry and an eccentric distance (r), and is obtained through the following equation:

$$|\vec{P}| = \frac{2\pi J(t_i - t_{i+1})}{gNt_{i+1}t_i^2 \sin\alpha}$$

Wherein, $\vec{P}$ is an imbalance vector, J is a rotational inertia, N is a number of constant angles by which the gantry rotates in one revolution, $t_i$ is a duration required for the gantry rotating by the ith constant angle, $t_{i+1}$ is a duration required for the gantry rotating by the (i+1)th constant angle, g is the acceleration of gravity, and α is the eccentric angle.

10. A device for balancing a Computed Tomography (CT) gantry, the CT gantry having a data collection unit for collecting data and a weight counterbalancing position for balancing the CT gantry, wherein the device comprises a processor in signal connection with the data collection unit; the data collection unit is configured to collect a fluctuation chain of pulses generated in one revolution of the gantry; the processor is configured to obtain an eccentric angle of a center of mass deviating from a rotation center according to the fluctuation chain, and calculate a magnitude of imbalance; and the processor is configured to adjust weight at the weight counterbalancing position according to the eccentric angle and the magnitude of imbalance, to locate the center of mass at the rotation center; and wherein a sampling is performed once each time the gantry rotates by a constant angle, a curve of a pulse generated in each sampling is obtained, and curves corresponding to respective angles in a rotational direction of the gantry are successively connected to form the fluctuation chain.

11. The device for balancing the CT gantry according to claim 10, further comprising a detector for detecting a rotation velocity of the gantry in real time, wherein the detector is in signal connection with the processor, and the processor is configured to adjust a torque voltage of a motor according to the rotation velocity of the gantry, to enable the rotation of the gantry to reach a steady state.

* * * * *